United States Patent [19]

Wattimena et al.

[11] Patent Number: 4,521,630
[45] Date of Patent: Jun. 4, 1985

[54] PROCESS FOR THE PREPARATION OF ALDEHYDES

[75] Inventors: Freddy Wattimena; Hendricus J. Heijmen, both of Amsterdam, Netherlands

[73] Assignee: Shell Oil Company, Houston, Tex.

[21] Appl. No.: 521,777

[22] Filed: Aug. 9, 1983

[30] Foreign Application Priority Data

Aug. 9, 1982 [GB] United Kingdom ............... 8222902

[51] Int. Cl.$^3$ ............................................. C07C 45/41
[52] U.S. Cl. .................... 568/435; 568/484; 568/424; 568/420; 260/465 B; 260/465.1
[58] Field of Search ............ 568/435, 484, 424, 420; 260/465 B, 465.1

[56] References Cited

U.S. PATENT DOCUMENTS 4,328,373 5/1982 Strojny ............................... 568/435

Primary Examiner—Bernard Helfin
Attorney, Agent, or Firm—Ronald R. Reper

[57] ABSTRACT

Aldehydes are prepared by hydrogenating a compound of general formula R'COOR, wherein R represents a hydrogen atom, an alkyl or an acyl group, or a metal, and R' represents an optionally substituted hydrocarbyl group having at most two alpha-hydrogen atoms, provided it has at most one beta-hydrogen atom, in case it has two alpha-hydrogen atoms, in the presence of a catalyst comprising at least one metal selected from rare earth metals and iron on an alumina-based carrier.

16 Claims, No Drawings

1

PROCESS FOR THE PREPARATION OF ALDEHYDES

BACKGROUND OF THE INVENTION

This invention relates to a process and a catalytic composition for the preparation of aldehydes, i.e. aliphatic or aromatic compounds containing one or more —CHO groups, and to the aldehydes thus prepared.

Aldehydes may be prepared in a few general ways. Because of their ready availability, carboxylic acids would be advantageous starting compounds for the preparation of aldehydes. However, as detailed e.g., by J. D. Roberts and M. J. Caserio, "Modern Organic Chemistry", New York 1967, p. 310, conversion of a carboxylic acid to an aldehyde by direct reduction is not easy to achieve because acids are generally difficult to reduce, whereas aldehydes are easily reduced. Thus the problem is to keep the reaction from going too far.

For instance, as far as known, only lithium aluminum hydride is capable of mildly reducing carboxylic acids, esters or anhydrides; however, the reduction products are alcohols instead of aldehydes.

The most useful known aldehyde preparation procedures involve conversion of an acid to a derivative that either is more easily reduced than an aldehyde, or else is reduced to a substance from which the aldehyde can be generated. The so-called Rosenmund reduction involves the first of these schemes; in this procedure the acid is converted to an acyl chloride, which is reduced with hydrogen over a palladium catalyst to the aldehyde. The rate of reduction of the aldehyde to the corresponding alcohol has to be kept at a low level by poisoning the catalyst with sulphur. Reduction of an acid to a substance that can be converted to an aldehyde is usefully achieved by way of lithium aluminum hydride reduction of the nitrile corresponding to the acid. The reduction step is usually successful only if inverse addition is used; i.e., a solution of LiAlH$_4$ has to be added to a solution of the nitrile, preferably at low temperatures, e.g., $-50°$ C., otherwise the reduction product is a primary amine. Clearly these known procedures are laborious, since they involve at least two steps, and usually more. Also, the use of chemicals like LiAlH$_4$ may be quite convenient in a laboratory synthesis, but its use is less desired in industrial scale preparations, where straightforward hydrogenation would be much preferred. It is desirable therefore to provide a process and a catalytic composition for the preparation of aldehydes from carboxylic acids, or close derivatives thereof, in one step. More specifically, it is the object of the present invention to provide a process and a catalytic composition for the preparation of aldehydes, comprising the reduction of carboxylic acids or esters, anhydrides or salts thereof by hydrogenation.

According to the invention this is achieved for certain compounds of the general formula R'COOR when employing an alumina-based catalyst containing one or more rare earth metals and iron.

SUMMARY OF THE INVENTION

Accordingly, the invention relates to a process for the preparation of aldehydes, by the reduction of carboxylic acids or esters, anhydrides or salts thereof which process comprises hydrogenating a compound of the general formula R'COOR, wherein R represents a hydrogen atom, an alkyl or an acyl group, or a metal, and R' represents an optionally substituted hydrocarbyl group having at most two alpha-hydrogen atoms, provided it has at most one beta-hydrogen atom, in case it has two alpha-hydrogen atoms, in the presence of a catalyst comprising a rare earth metal and iron on an alumina-based carrier.

DESCRIPTION OF PREFERRED EMBODIMENTS

The present invention provides an easy, one step catalytic conversion of carboxylic acids and derivatives into the aldehydes. Surprisingly it has been found that the further hydrogenation of the aldehyde to the alcohol does not take place in the present process. Why this is so, is not understood; it is thought however, that the catalyst prevents the formation of alcohols or intermediate products by forming particular transitionary complexes with the carboxylate and the aldehyde group.

The compound R'COOR, when R represents a hydrogen atom, is a carboxylic acid, and when R represents an alkyl or an acyl group, in particular having up to 20 carbon atoms, the said compound obviously is an ester or an aldehyde (which may be mixed). R may also represent a metal e.g., of Groups I to III and/or VIII, since these metals generally are capable of forming carboxylate salts. These groups include both the even series (main groups, A family) and the odd series (subgroups, B family). For instance, alkali metals, alkaline earth metals, rare earth metals, the iron and the platinum group metals, copper, silver, zinc cadmium, mercury, aluminum, gallium and indium are suitable. Preferably a carboxylic acid of the formula R'COOH is hydrogenated, since such a compound is more readily available, generally, than the derivatives thereof.

The group represented by R' is an aliphatic or aromatic hydrocarbyl group, which may be optionally substituted, since it is known that the presence of substituents does not substantially influence the properties of the carboxylate group. Thus the hydrocarbyl group may be substituted with e.g., halogen, cyano, hydroxy, nitro, nitroso, amino, thio and/or oxo-groups. The hydrocarbyl group should have at most one alpha-hydrogen atom, which means that at most one hydrogen atom is connected to the carbon atom of the hydrocarbyl group that is connected to the carbon atom of the hydrocarbyl group that is connected with the carboxylate group, or—when this is not the case—it should have at most one beta-hydrogen atom, which means that at most one hydrogen atom is connected to the carbon atom of the hydrocarbyl group that is connected to the CH$_2$ group linked to the carboxylate group. The hydrocarbyl group represented by R' preferably has at least three carbon atoms, e.g., isopropyl or cyclopropyl, and in particular it contains from 3 to 20 carbon atoms. More particularly it contains from 4 to 10 carbon atoms, being e.g., sec.butyl, p.tolyl, or benzyl. The carboxylic acids formed with the latter three hydrocarbyl groups are called trivially: isovaleric, p.toluic and phenylacetic acid, respectively.

It appears that compounds of formula R'COOR, wherein R' is not as defined according to the invention, do not yield aldehydes in appreciable quantities. In fact, the main product mostly is the ketone formed by a decarboxylative condensation of two carboxylic acids: R'C(O)R'. If the group represented by R' contains one alpha- or beta-hydrogen atom, this ketone is also formed to a certain extent, but aldehydes are already present in substantial amounts in the products. The best results are obtained when R' represents a hydrocarbyl group having at most two alpha-hydrogen atoms, provided it has no beta-hydrogen atoms, in case it has one or two alpha hydrogen atoms. Yields of up to 100% are possible in this case.

Preferably R' represents a branched alkyl group of structure

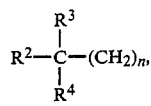

in which $R^2$, $R^3$ and $R^4$ each independently represent an alkyl group (in particular containing 1 to 3 carbon atoms), and in which $n=0$ or 1. In particular R' represents a tertiary butyl group, i.e., the group of the above structure wherein $R^2=R^3=R^4=CH_3$ and $n=0$. The carboxylic acid corresponding herewith, pivalic acid, may be hydrogenated quantitatively to pivalaldehyde (2,2-dimethylpropanal).

In an alternative embodiment, R' represents an aryl or alkaryl group. For instance, R' may represent a phenyl group, R'COOH thus being benzoic acid, a tolyl group (a toluic acid), a xylyl group (a xylylic acid, e.g., hemellitic, mesitylenic or isoxylylic acid), or a cumenyl group (a cuminic acid, e.g., cumic acid). Advantageously, the alkaryl group is a p.tert.butylphenyl group, R'COOH thus being p.tert.butyl benzoic acid.

The catalyst used in the process according to the invention contains one or more rare earth metals and iron. Suitably the catalyst contains up to 30%w, advantageously from 5 to 30%w and preferably from 10 to 25%w of rare earth metal, based on the weight of the carrier. In addition hereto, the catalyst suitably contains up to 20%w, advantageously from 0.1 to 20%w and preferably from 0.5 to 10%w of iron, based on the weight of the carrier. Although these amounts refer to metals, these elements are present mostly as compounds, e.g., as oxides, sulphides and the like. Preferably the metal(s) is (are) present as oxide(s).

The carrier is based on alumina, $Al_2O_3$, and ma contain minor amounts of other known carrier materials. The expression "based on alumina" as used herein means that the carrier should consist of $Al_2O_3$ for at least 50% by weight. It has been observed, however, that the presence of other carrier materials such as silica, is detrimental to the selectivity towards aldehyde formation, and therefore it is most preferred to employ a pure alumina as carrier material. In particular the alumina-based carrier consists of gamma-alumina. Aluminas may have a specific surface area in the range of 0.01 to 400 $m^2g$, the gamma-aluminas having a specific surface area of 25 to 350 $m^2g$.

In order to be able to increase the content of metal, and thus to obtain a higher catalytic activity, it is advantageous to use a carrier material with a large specific surface area. Excellent results have been obtained with the alumina having a specific surface area of 125 to 260 $m^2/g$. Such aluminas are commercially available, both for fluid and for fixed bed application.

The rare earth metals comprise the elements scandium, yttrium, lanthanum and the lanthanides, i.e., the elements having atomic numbers 58 to 71 inclusive. The rare earth elements often are found together and are rather difficult to separate. Conveniently, therefore, sometimes mixtures of rare earth elements in naturally occurring ratios are used, without determining which element actually is the most active catalyst.

Very satisfactory results have been obtained when as rare earth metal lanthanum, cerium, praeseodymium and/or neodymium is used. A mixture of rare earth elements excluding cerium is commercially obtainable—at a low price—under the name of didymium, and excellent results have been obtained herewith. Preferably therefrom a mixture of (at least) lanthanum, praesedodymium and neodymium in a naturally occurring ratio is used as rare earth [please refer to Kirk-Othmer, Encyclopedia of Chemical Technology (1968), Vol. 17, p. 147, for more information on rare earth mixtures].

The rare earth metal or metals and the iron may be incorporated in the carrier by any convenient method, for example by impregnation of aqueous solutions of decomposable salts, e.g., acetates or nitrates. Suitably the impregnated carrier is dried and calcined in order to form the oxides. The calcination is effected preferably at a temperature in the range from 350° to 600° C., for a period of up to 4 hours. It is also possible to use the catalyst without prior calcination. In that case a catalyst containing metal-carboxylate salts is formed during the reaction.

The catalytic action of the catalyst may be improved by adding one or more elements as a promoter to the catalyst, especially if the catalyst contains rare earth metal(s). In particular these promoters are chosen from the group of elements known as the transition metal, e.g., those elements contained in Groups IB to VIIB and VIII of the Periodic System of the Elements, as presented e.g., on the last page of R. C. Weast (ed.), Handbook of Chemistry and Physics, The Chemical Rubber Co., Cleveland, Ohio. Alternatively the promoters may be chosen from selenium and the elements contained in Groups IA, IIA and IIIA. Preferably the catalyst contains one or more promoting metals of Groups II, III and/or VIII in addition to rare earth metals(s). The word "metals" excludes boron of course. Groups III and VIII include a few elements already possible present in the catalyst, e.g., aluminum and the rare earth elements and iron (in the carrier and as the catalytic metals, respectively), so these are also precluded from being added as a promoter. Excellent results are obtained when the promoting metal(s) of Groups II, III and/or VIII is (are) magnesium, zinc, cadmium, gallium and/or cobalt. The quantity of the promoting metals may vary between rather wide limits, but advantageously the atomic ratio of the combined promoting metal(s) of Groups II, III and/or VIII to the combined rare earth metal(s) lies between 0.05 and 1.0, and particularly between 0.1 and 0.5.

Advantageously the catalyst contains both iron and one or more rare earth metals. It has appeared that in that case the catalyst activity and selectivity can be adjusted by varying the total amount and the relative proportion, respectively, of the iron and the rare earth metal(s). For instance, at a constant ratio of iron to rare earth, the catalyst activity, i.e., the carboxylic acid conversion, increases at increasing metal loading. However, above 0.2 gram atoms (gat) of metal per 100 g of carrier the catalytic activity does not substantially increase anymore, whereas below 0.01 gat/100 g it becomes rather low. Preferably therefore the total amount of iron and rare earth metal(s) lies between 0.01 and 0.2 gat/100 g of carrier. It has also appeared that at a constant metal loading, provided it is expressed in gram atoms, the catalyst selectivity increases with increasing rare earth metal to iron ratios. For high selectivities the catalyst should preferably have an iron to rare earth metal atomic ratio below 4.0. The iron content, and thus the activity, may become too low, however, at values below 0.05 for said ratio. Thus the iron to rare earth metal atomic ratio preferably lies between 0.05 and 4.0, and particularly between 0.1 and 2.5. Conversions of up to 100% are possible by increasing the iron content of the catalyst, whereas selectivities of up to 100% have been obtained by increasing the rare earth metal proportion.

The most preferred composition comprises about 5.9 g iron and 7.2 g rare earth metal per 100 g of carrier, which corresponds with roughly 0.16 gat/100 g of carrier and an atomic ratio of iron to rare earth of about 2.1.

The actual hydrogenation reaction is preferably carried out by passing the reactants over the catalyst, either in a fixed, in a moving or in a fluidized bed. Advantageously the process is carried out in a fluidized bed. The catalyst and/or the reactants may have been preheated to a suitable reaction temperature, advantageously to at least the vaporization temperature of the carboxylic acid or the derivatives thereof, e.g., to a temperature of 100° to 400° C.

The hydrogenation could be carried out using hydrogen generated in situ, e.g., by the dehydrogenation of methanol or other alcohols, but preferably hydrogen gas or a mixture of gases containing hydrogen gas is used. In particular the compound of general formula R'COOR is hydrogenated using hydrogen gas in a molar ratio of more than 0.1 to the said compound, preferably of from 1.0 to 10.

The preparation, i.e., the actual hydrogenation, is carried out at a temperature of preferably 250° to 550° C., particularly 400° to 500° C. Advantageously the preparation is carried out at a weight hourly space velocity of 0.1 to 4.0 kg/kg/h, i.e., kg of carboxylic acid or ester, anhydride or salt thereof per kg of catalyst per hour. In particular the space velocity is from 0.2 to 2.0 kg/kg/h.

The reactants may be used per se, or diluted with an inert gas such as nitrogen or argon. Air is not inert. Steam or water may be added to the feed to effect the hydrolysis of anhydrides into the corresponding carboxylic acids, which are subsequently reduced to the aldehydes, and to minimize the formation of carbonaceous material on the catalyst. Suitably an inert solvent is used to facilitate the dosage of any solid starting materials. Toluene or benzene is very suitable.

The pressure used may be atmospheric pressure or above, e.g., from 1 to 20 atm.

The present application also relates to aldehydes whenever prepared by a process according to the invention, and to a catalytic composition, comprising one or more rare earth metals and/or iron on an alumina-based carrier, in particular comprising both rare earth metal(s) and iron on an alumina-based carrier.

The aldehydes formed may find industrial application as intermediates for aroma chemicals production, or as aroma chemicals themselves.

EXAMPLES

The following Examples illustrate the invention. The identity of the products was confirmed by infra-red and nuclear magnetic resonance (nmr) analysis and by gas-liquid chromatography as necessary.

All catalysts were prepared by adding a solution of the metal nitrate(s) in water to alumina in an amount equal to its pore-volume, and removing the water in the pores by stirring the mixture at about 100°–150° C. Then the catalysts were calcined in air at 500° C. for 2 hours. All catalyst compositions are given in pbw of metal per 100 parts of carrier. The carrier material was a gamma-alumina, E-type, i.e., a carrier metal suitable for use in fluid beds, having a specific surface area of 125 m$^2$/g and manufactured by Ketjen. In all experiments 12 ml of calcined catalyst were transferred to a micro-fluid-bed reactor. A mixture of a carboxylic acid and toluene (solvent), at atmospheric pressure, was fed through the catalyst a various temperatures (T, °C.), hydrogen/acid ratios, and various weight hourly space velocities (WHSV, kg/kg/hour). This corresponded generally to a contact time of 1–5 seconds. The conversion of acid and the yield of aldehyde were measured by gas liquid chromatography and nmr analysis.

EXAMPLE I

The reduction of pivalic acid (PAC) to pivalaldehyde (PAL) was performed using a catalyst comprising 17.2 parts by weight neodymium on 100 parts by weight alumina. The neodymium was present as the oxide, at least intially.

The results are tabulated below.

TABLE I

| Experiment No. | T °C. | mol. ratio H$_2$/PAC | WHSV PAC kg/kg/h | Conv. PAC % | Yield PAL mol. % |
|---|---|---|---|---|---|
| 1 | 444 | 3/1 | 0.33 | 32 | 25 |
| 2 | 456 | 3/1 | 0.33 | 44 | 37 |
| 3 | 465 | 3/1 | 0.33 | 52 | 51 |
| 4 | 480 | 3/1 | 0.33 | 70 | 63 |
| 5 | 465 | 3/1 | 0.66 | 36 | 34 |
| 6 | 480 | 3/1 | 0.66 | 52 | 51 |
| 7 | 456 | 5/1 | 0.33 | 54 | 54 |
| 8 | 456 | 7/1 | 0.33 | 62 | 62 |
| 9 | 446 | 7/1 | 0.33 | 53 | 44 |
| 10 | 470 | 7/1 | 0.33 | 77 | 77 |

From these experiments it is clear, that increasing the temperature or the hydrogen/pivalic acid ratio, or decreasing the space velocity (WHSV), generally improves the conversion and the yield.

Temperatures above 600° C. are not practical, since too much decomposition takes place and consequently the yield of desired aldehyde decreases.

EXAMPLE II

Example I was repeated using catalysts containing various rare earth metals and, for comparative purposes, thorium. Di stands for didymium, a commercially obtainable mixture of rare earth metals, the oxide, Di$_2$O$_3$, having the following composition by weight 45.8% LA$_2$O$_3$, 9.5% Pr$_6$O$_{11}$, 32.5% Nd$_2$O$_3$, 5.5% Sm$_2$O$_3$, 3.5% Gd$_2$O$_3$, 0.5% Y$_2$O$_3$, and 2.7% other rare earth oxides. In all experiments the hydrogen/pivalic acid molar ratio was 5/1, and the gaseous hourly space velocity was kept at 550 l acid vapor/1 catalyst/hour—except in experiment 7.

The results are tabulated below.

TABLE II

| Experiment No. | Metal pbw on 100 Al$_2$O$_3$ | T °C. | GHSV PAC 1/l/h | Conv. PAC % | Selectivity PAL mol. % |
|---|---|---|---|---|---|
| 11 | 16.5 Di | 476 | 550 | 90 | 80 |

TABLE II-continued

| Experiment No. | Metal pbw on 100 Al$_2$O$_3$ | T °C. | GHSV PAC 1/1/h | Conv. PAC % | Selectivity PAL mol. % |
|---|---|---|---|---|---|
| 12 | 17.2 Ce | 466 | 550 | 85 | 84 |
| 13 | 17.2 La | 446 | 550 | 64 | 95 |
| 7 | 17.2 Nd | 456 | 574 | 54 | 100 |
| a* | 17.2 Th | 481 | 550 | 71 | 4 |

*Comparative.

These data illustrate that the rare earth metals have suitable catalytic properties, but that the related actinide, thorium, does not: the main product formed was not identified further. The use of cobalt, zinc or nickel on alumina equally did hardly yield aldehydes.

EXAMPLE III

Example II was repeated using catalysts containing various amounts of didymium. Again the molar ratio of hydrogen to pivalic acid was 5/1, whereas the GHSV was 550 1/1/h in all experiments.

TABLE III

| Experiment No. | Di pbw | T °C. | Conv. PAC, % | Selectivity PAL, mol. % |
|---|---|---|---|---|
| 14 | 10 | 452 | 54 | 63 |
| 15 | 10 | 466 | 69 | 68 |
| 16 | 10 | 480 | 82 | 73 |
| 17 | 15 | 456 | 49 | 98 |
| 18 | 15 | 471 | 69 | 89 |
| 19 | 15 | 486 | 86 | 91 |
| 20 | 16.5 | 449 | 67 | 58 |
| 21 | 16.5 | 461 | 54 | 98 |
| 11 | 16.5 | 476 | 90 | 80 |
| 22 | 20 | 452 | 68 | 75 |
| 23 | 20 | 462 | 77 | 82 |
| 24 | 20 | 471 | 85 | 89 |
| 25 | 20 | 481 | 92 | 90 |

From these data it may be concluded that the D-content of the catalyst should preferably be at least 15 pbw per 100 parts of carrier (Al$_2$O$_3$), but that lesser contents can be used too.

EXAMPLE IV

The reduction of several carboxylic acids and esters to the corresponding aldehydes was performed, using a catalyst containing 26 pbw Di, 1 pwb Cu and 2 pbw Cr on 100 pbw of carrier, except where indicated otherwise. The carrier used was the same as the carrier in Example I, a gamma-alumina, E-type. The reaction conditions were chosen to illustrate the (im)possibility of the reaction according to the invention using different starting compounds, but no quantitative conclusions can be drawn regarding the relative conversions and selectivities from the experiments presented below.

TABLE IV

| Exp. No. | acid (derivative) | H-atoms α | H-atoms β | T °C. | GHSV acid 1/1/h | H$_2$/acid(der.)/ toluene (molar ratio) | Conv. % | Aldehyde select. mol. % |
|---|---|---|---|---|---|---|---|---|
| 26 | p.tert/butyl-benzoic acid | 0 | 2 | 400 | 1400 | 40/1/20 | 100 | 80 |
| 27 | methyl p.toluate | 0 | 2 | 450 | 1400 | 10/1/4 | 100 | 84 |
| 28 | isobutyric acid** | 1 | 6 | 429 | 625 | 8/1/0.25 | 88 | 28 |
| 29 | 3,3-dimethyl-butanoic acid | 2 | 0 | 425 | 1400 | 8/1/3 | 95 | 86 |
| 30 | methyl 3,3-dimethyl-butanoate | 2 | 0 | 425 | 1400 | 8/1/3 | 80 | 75 |
| 31 | isovaleric acid | 2 | 1 | 475 | 1400 | 8/1/1 | 80 | 13 |
| 32 | 3-methyl heptanoic acid | 2 | 1 | 425 | 1400 | 25/1/12 | 100 | 10 |
| 33 | pivalic acid anhydride** | 0 | 9 | 473 | 767 | 7.7/1/0.9 | 80 | 44 |
| b* | 4-methyl heptanoic acid | 2 | 2 | 425 | 1400 | 9/1/3 | 92 | 0 |
| c* | n-octanoic acid | 2 | 2 | 425 | 1400 | 8/1/3 | 79 | 0 |
| d* | acetic acid*** | 3 | — | 404 | 933 | 5/1/0.2 | 100 | 0 |
| e* | propionic acid*** | 2 | 3 | 427 | 767 | 5/1/0.2 | 100 | 0 |

*comparative
**catalyst containing 15 pbw Di only
***catalyst containing 17.2 pbw La only Apparently the compounds containing no alpha or beta hydrogen atoms (nrs 26, 27, 29,, 30) are most suitable for the present reaction; and the compounds having one alpha-hydrogen atoms (nr. 28) or two alpha and one beta-hydrogen atom (nrs. 31, 32) also yield appreciable, but decreasing quantities of aldehyde. However, the carboxylic acids having two alpha- and two beta-hydrogen atoms, or three alpha-hydrogen atoms, either branched (b) or straight-chain (c, d, e), cannot be reduced to aldehydes. In fact, they yield mainly the ketone resulting from the decarboxylative condensation of two carboxylic acids—a reaction which also takes place in the absence of hydrogen.

EXAMPLE V

The effect of various metals which act as promoters was studied, using as base case experiment 17 of Example III, i.e., and Al$_2$O$_3$ (gamma, E-type) carrier, containing 15 pbw Di on 100 pbw of carrier, a molar ratio hydrogen/pivalic acid kept constant at 5/1, and a GHSV kept constant at 550 1/1/h. The amount of promoter added was 19% molar, calculated on Di, in all experiments.

TABLE V

| Exp. No. | metal pbw | T °C. | Conv. PAC, % | Selectivity PAL, mol. % | Yield PAL, mol. % |
|---|---|---|---|---|---|
| 17 | — | 456 | 49 | 98 | 48 |
| 34 | 0.5 Mg | 457 | 64 | 99 | 63 |
| 35 | 1.3 Zn | 456 | 75 | 100 | 75 |
| 36 | 2.2 Cd | 455 | 60 | 89 | 54 |
| 37 | 1.4 Ga | 457 | 61 | 93 | 57 |
| 38 | 1.2 Co | 457 | 58 | 100 | 58 |
| 39* | 1.6 Se | 457 | 48 | 98 | 47 |
| 40* | 2.1 Ag | 457 | 93 | 47 | 43 |

*GHSV = 793 1/1h. H$_2$/PAC ratio = 4.2/1

Experiments 39 and 40 illustrate the yield promoting effect of selenium and silver, taking into account the higher space velocity and the lower hydrogen/pivalic acid ratio. Similar promoting effects were found using 4.0 Hg, 2.3 In, 4/1 Pg, 1.0 Cr and 1.9 Mo; these catalyst however are less preferred, because they appear to be unstable in activity and/or selectivity after a certain period of use.

EXAMPLE VI

The reduction of pivalic acid to pivaldehyde was studied using a number of iron-containing catalysts, and—for comparative proposes—a cobalt- and a nickel-containing catalyst. The GHSV was 793 1/1/h, and the hydrogen pivalic acid molar ratio was kept at 4.2. The results are collected in Table VI.

TABLE VI

| Exp. No. | metal pbw | T °C. | Conv. % | Selectivity % molar | Yield % molar |
|---|---|---|---|---|---|
| 41 | 2.8 Fe | 457 | 32.8 | 72.3 | 23.7 |
| 42 | 6 Fe | 457 | 57.6 | 85.6 | 49.3 |
| 43 | 8.7 Fe | 444 | 62.1 | 87.0 | 54.0 |
| 44 | 11.8 Fe | 444 | 79.9 | 80.7 | 64.5 |
| f* | 8.84 Co | 444 | 92.3 | 10.4 | 9.6 |
| g* | 8.8 Ni | 444 | 86.5 | 4.4 | 3.8 |

*Comparative

It may be concluded, that the iron-containing catalysts, especially those containing more than 5 pbw per 100 pbw carrier, are suitable for the reduction of pivalic acid towards pivalaldehyde, but that the (closely related) cobalt- and nickel-containing catalysts hardly catalyse the desired reaction.

EXAMPLE VII

Example VI was repeated using a number of catalysts containing both iron and didymium, ie.e, the rare earths mixture of Example II, at a temperature of 457° C. Table VII shows the results.

TABLE VII

| Experiment No. | Fe g/100 g Al$_2$O$_3$ | Di g/100 g Al$_2$O$_3$ | Fe + Di gat/100 g Al$_2$O$_3$ | Fe:Di atomic ratio | Conversion % | Yield % mol. | Selectivity % mol. |
|---|---|---|---|---|---|---|---|
| 45 | 0.6 | 15 | 0.116 | 0.10 | 39.2 | 39.1 | 99.6 |
| 46 | 1.1 | 15 | 0.125 | 0.19 | 45.5 | 45.5 | 100 |
| 47 | 2.8 | 15 | 0.156 | 0.47 | 64.0 | 63.4 | 99.2 |
| 48 | 5.9 | 15 | 0.211 | 1.00 | 82.0 | 78.4 | 95.6 |
| 49 | 5.9 | 7.2 | 0.156 | 2.08 | 75.3 | 69.4 | 92.2 |
| 50 | 6.7 | 8.6 | 0.180 | 1.98 | 73.3 | 73.3 | 100 |
| 51 | 1.1 | 12.3 | 0.106 | 0.23 | 47.0 | 44.5 | 94.7 |
| 52 | 2.8 | 8.0 | 0.106 | 0.89 | 50.8 | 47.2 | 93.0 |
| 53 | 4.8 | 2.9 | 0.106 | 4.20 | 55.5 | 48.6 | 87.6 |
| 54 | 5.9 | 2.9 | 0.147 | 5.15 | 63.7 | 44.2 | 57.1 |

The catalysts having a Fe:Di atomic ratio above 4 (numbers 53 and 54), show the relatively lowest selectivity, whereas the catalysts having said ratio below 0.40 (numbers 45, 46, 51) show the relatively lowest conversion. It is evident from the series of catalysts having the same metal content expression in gram atoms (numbers 47 and 49; numbers 51, 52 and 53), that increasing the Fe:Di ratio improves the conversion while lowering the selectivity. Although catalyst number 48 shows the best conversion and yield figures of the Table, it is not the most preferred catalytic composition, since it appeared that other compositions, which have a total metal content below 2.0 gat/100 g Al$_2$O$_3$, are somewhat more stable during prolonged use. For this reason the most preferred catalytic composition for the reduction of pivalic acid is catalyst number 49.

We claim:

1. Process for the preparation of aldehydes, by the reduction of carboxylic acids or esters, anhydrides or salts thereof, which comprises hydrogenating as feed at least one compound of the general formula R'COOR, wherein R represents a hydrogen atom, an alkyl or an acyl group, or a metal and R' represents an optionally substituted hydrocarbyl group having at most two alpha-hydrogen atoms, provided it has at most one beta-hydrogen atom, in case it has two alpha-hydrogen atoms, in a reaction zone at a temperature of 250° to 550° C. a weight hourly space velocity of 0.1 to 4.0 kg/kg/h and a molar ratio of hydrogen gas to feed compound of more than 0.1 in the presence of a catalyst comprising at least one rare earth metal and iron on a gamma-alumina carrier, wherein the total amount of iron and rare earth metals lies between 0.01 and 0.2 gat/100 g of carrier and the atomic ratio of iron to rare earth metal lies between 0.4 and 4.0; and separating an aldehyde-containing product from said reaction zone.

2. A process as in claim 1, wherein said compound of the formula R'COOR is a carboxylic acid.

3. A process as in claim 1, where in R represents an alkyl or an acyl group having up to 20 carbon atoms.

4. A process as in claim 1, wherein in the feed compound, the group represented by R' contains from 3 to 20 carbon atoms.

5. A process as in claim 1, wherein R' represents a hydrocarbyl group having at most two alpha-hydrogen atoms, provided it has no beta-hydrogen atoms, in case it has one or two alpha-hydrogen atoms.

6. A process as in claim 5, wherein in the feed compound formula, R' represents a branched alkyl group of structure

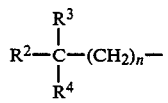

in which R$^2$, R$^3$ and R$^4$ each independently represent an alkyl group, and n is 0 or 1.

7. A process as in claim 6, wherein R'0 represents a tertiary butyl group.

8. A process as in claim 1, wherein R' represents an aryl or alkaryl group.

9. A process as in claim 1, wherein the gamma-alumina carrier has a specific area of 125 to 260 m$^2$/g.

10. A process as in claim 1, wherein the catalyst contains at least one rare earth metal selected from the group consisting of lanthanum, cerium, praeseodymium and neodymium.

11. A process as in claim 1, wherein at least one catalyst metal is present as oxide.

12. A process as in claim 1, wherein the catalyst contains at least one promoting metal of Groups II, III and/or VIII.

13. A process as in claim 12, wherein the promoting metal of Groups II, III and/or VIII is at least one of magnesium, zinc, cadmium, gallium and cobalt.

14. A process as in claim 12, wherein the atomic ratio of the combined promoting metal of Groups II, III and/or VIII to the combined rare earth metal lies between 0.05 and 1.0.

15. A process as in claim 1, wherein during hydrogenation the molar ratio of hydrogen gas to the feed compound lies between 1.0 and 10.

16. A process in claim 1, wherein the hydrogenation is carried out at a weight hourly space velocity of 0.2 to 2.0 kg/kg/h.

* * * * *